US012426858B2

(12) United States Patent
Clements et al.

(10) Patent No.: US 12,426,858 B2
(45) Date of Patent: *Sep. 30, 2025

(54) IN-BED TEMPERATURE ARRAY FOR MENSTRUAL CYCLE TRACKING

(71) Applicant: Apple Inc., Cupertino, CA (US)

(72) Inventors: James C. Clements, Campbell, CA (US); Erno H. Klaassen, Los Altos, CA (US); Habib S. Karaki, Sunnyvale, CA (US); Joseph M. Schmitt, Santa Clara, CA (US); Zijing Zeng, San Jose, CA (US)

(73) Assignee: Apple Inc., Cupertino, CA (US)

( * ) Notice: Subject to any disclaimer, the term of this patent is extended or adjusted under 35 U.S.C. 154(b) by 114 days.

This patent is subject to a terminal disclaimer.

(21) Appl. No.: 18/234,804

(22) Filed: Aug. 16, 2023

(65) Prior Publication Data

US 2023/0389899 A1 Dec. 7, 2023

Related U.S. Application Data

(63) Continuation of application No. 16/991,815, filed on Aug. 12, 2020, now Pat. No. 11,771,406.

(51) Int. Cl.
*A61B 5/00* (2006.01)
*A61B 5/01* (2006.01)
(Continued)

(52) U.S. Cl.
CPC .......... *A61B 10/0012* (2013.01); *A61B 5/01* (2013.01); *A61B 5/6892* (2013.01);
(Continued)

(58) Field of Classification Search
CPC ..... A61B 10/0012; A61B 5/01; A61B 5/6892; A61B 2010/0019; A61B 2562/0271;
(Continued)

(56) References Cited

U.S. PATENT DOCUMENTS 4,148,304 A * 4/1979 Mull .................. A61B 10/0012
374/E13.002
4,151,831 A * 5/1979 Lester .................. G04B 47/061
368/251
(Continued)

FOREIGN PATENT DOCUMENTS

CN 107529986 1/2018
CN 108784748 11/2018
(Continued)

*Primary Examiner* — May A Abouelela
(74) *Attorney, Agent, or Firm* — Brownstein Hyatt Farber Schreck, LLP

(57) ABSTRACT

Embodiments are directed to systems and techniques for tracking menstrual cycles, which can include receiving temperature measurements from an array of temperature sensors positioned on a bed. A use period for the array can be determined when temperature measurements from at least one temperature sensor of the one or more temperature sensors exceed a first temperature threshold. In some embodiments, for each use period in a set of two or more use periods, a temperature of the user using the set of temperatures from the respective use period can be determined. After determining the temperature of the user for each use period in the set of two or more use periods, at least one change in the temperature of the user between different use periods can be identified. An ovulation day of the user based on the at least one change in the temperature of the user can be estimated.

15 Claims, 6 Drawing Sheets

(51) Int. Cl.
*A61B 10/00* (2006.01)
*G01K 7/01* (2006.01)
*G01K 7/02* (2021.01)
*G01K 7/16* (2006.01)

(52) U.S. Cl.
CPC ............... *A61B 2010/0019* (2013.01); *A61B 2562/0271* (2013.01); *A61B 2562/043* (2013.01); *G01K 7/01* (2013.01); *G01K 7/02* (2013.01); *G01K 7/16* (2013.01)

(58) Field of Classification Search
CPC .......... A61B 2562/043; A61B 2562/04; A61B 2562/164; G01K 7/01; G01K 7/02; G01K 7/16; G01K 1/024; G01K 1/026
See application file for complete search history.

(56) References Cited

U.S. PATENT DOCUMENTS

| | | | | |
|---|---|---|---|---|
| 4,443,851 A * | 4/1984 | Lin | | G04G 21/025 374/102 |
| 4,465,077 A * | 8/1984 | Schneider | | G01K 7/24 706/924 |
| 4,515,167 A * | 5/1985 | Hochman | | A61B 10/0012 607/70 |
| 4,557,273 A * | 12/1985 | Stoller | | A61B 10/0012 600/382 |
| 4,865,044 A * | 9/1989 | Wallace | | G01K 3/14 374/E1.004 |
| 5,209,238 A * | 5/1993 | Sundhar | | A61B 10/0012 600/551 |
| 5,216,599 A * | 6/1993 | Uebe | | A61D 17/002 128/920 |
| 5,657,762 A * | 8/1997 | Coley | | A61B 10/0012 600/549 |
| 8,328,420 B2 | 12/2012 | Abreu | | |
| 8,374,989 B2 | 2/2013 | Lee et al. | | |
| 8,540,644 B2 | 9/2013 | Husheer | | |
| 8,834,389 B2 * | 9/2014 | Schafer | | G16H 40/63 600/551 |
| 8,992,822 B2 | 3/2015 | Filzwieser et al. | | |
| 9,131,891 B2 | 9/2015 | Shinar et al. | | |
| 9,572,647 B2 | 2/2017 | Couse et al. | | |
| 9,743,913 B2 | 8/2017 | Dillen | | |
| 9,867,597 B1 * | 1/2018 | Buard | | A61B 5/02438 |
| 10,060,802 B1 * | 8/2018 | Ragosta | | G01K 1/022 |
| 10,108,325 B2 * | 10/2018 | Hay | | G06F 16/7335 |
| 10,123,732 B2 | 11/2018 | Abreu | | |
| 10,172,593 B2 | 1/2019 | Shinar et al. | | |
| 10,194,810 B2 | 2/2019 | Halperin et al. | | |
| 10,278,638 B2 | 5/2019 | Dusanter et al. | | |
| 10,321,897 B2 * | 6/2019 | Kersken | | A61B 5/6847 |
| 10,383,523 B2 | 8/2019 | Yao | | |
| 10,575,829 B2 | 3/2020 | Shinar et al. | | |
| 10,765,409 B2 | 9/2020 | Lafon et al. | | |
| 10,779,802 B2 | 9/2020 | Tholen et al. | | |
| 10,973,495 B2 | 4/2021 | Vardi et al. | | |
| 11,209,957 B2 * | 12/2021 | Dryer | | G06F 3/04847 |
| 11,224,344 B2 | 1/2022 | Ellis et al. | | |
| 11,328,152 B2 | 5/2022 | Chen et al. | | |
| 11,439,370 B2 | 9/2022 | Bongiorno et al. | | |
| 11,517,292 B2 | 12/2022 | Stein et al. | | |
| 2004/0081024 A1 * | 4/2004 | Weng | | A61B 10/0012 368/10 |
| 2005/0010128 A1 * | 1/2005 | Shiraishi | | G01N 33/76 600/551 |
| 2005/0257822 A1 | 11/2005 | Smith et al. | | |
| 2008/0071190 A1 * | 3/2008 | Gorodeski | | A61B 10/0012 600/551 |
| 2009/0105605 A1 * | 4/2009 | Abreu | | A61B 5/0075 600/549 |
| 2009/0234200 A1 * | 9/2009 | Husheer | | A61B 5/0008 600/301 |
| 2010/0036279 A1 * | 2/2010 | Rieth | | A61B 5/4277 600/551 |
| 2010/0152606 A1 * | 6/2010 | Menashe | | A61B 5/01 600/549 |
| 2010/0191696 A1 * | 7/2010 | Lee | | A61B 10/0012 706/52 |
| 2012/0016258 A1 * | 1/2012 | Webster | | G01K 1/024 600/549 |
| 2012/0238900 A1 * | 9/2012 | Rechberg | | A61B 5/0008 600/549 |
| 2012/0265032 A1 * | 10/2012 | Ben-David | | A61B 5/01 600/549 |
| 2013/0137940 A1 * | 5/2013 | Schafer | | A61B 10/0012 600/301 |
| 2014/0247136 A1 * | 9/2014 | Proud | | G08C 17/02 709/224 |
| 2015/0133744 A1 * | 5/2015 | Kobayashi | | A61B 5/0022 600/301 |
| 2015/0148681 A1 * | 5/2015 | Abreu | | A61B 5/6821 600/474 |
| 2015/0164409 A1 | 6/2015 | Benson et al. | | |
| 2015/0182322 A1 * | 7/2015 | Couse | | G01K 1/20 119/858 |
| 2015/0190087 A1 * | 7/2015 | Shinar | | A61B 5/7282 600/595 |
| 2015/0289768 A1 * | 10/2015 | Toriumi | | A61B 5/746 340/588 |
| 2016/0015314 A1 * | 1/2016 | Dusanter | | A61B 5/4818 600/301 |
| 2016/0058428 A1 * | 3/2016 | Shinar | | A61B 5/7267 600/301 |
| 2016/0058429 A1 * | 3/2016 | Shinar | | A61B 5/4809 600/551 |
| 2016/0341603 A1 * | 11/2016 | Kusukame | | F24F 11/00 |
| 2017/0000347 A1 * | 1/2017 | Meftah | | A61B 5/02 |
| 2017/0007214 A1 * | 1/2017 | Dillen | | A61B 5/1118 |
| 2017/0128052 A1 * | 5/2017 | Han | | A61B 5/681 |
| 2017/0281017 A1 * | 10/2017 | Halperin | | A61B 5/0816 |
| 2018/0035982 A1 * | 2/2018 | Tholen | | A61B 10/0012 |
| 2018/0153413 A1 * | 6/2018 | Yao | | A61B 5/4812 |
| 2018/0214028 A1 * | 8/2018 | Zhang | | A61B 5/4318 |
| 2018/0242850 A1 * | 8/2018 | Ellis | | A61B 5/02007 |
| 2018/0267338 A1 * | 9/2018 | Hoggarth | | A61B 5/6821 |
| 2018/0325498 A1 * | 11/2018 | Bongiorno | | A61B 5/7282 |
| 2019/0021701 A1 * | 1/2019 | Vardi | | A61B 5/0008 |
| 2019/0110692 A1 * | 4/2019 | Pardey | | A61B 10/0012 |
| 2019/0110738 A1 * | 4/2019 | Baber | | A61B 5/01 |
| 2019/0133088 A1 * | 5/2019 | Hurley | | A61B 5/11 |
| 2019/0167236 A1 * | 6/2019 | Maas | | A61B 5/103 |
| 2019/0167237 A1 * | 6/2019 | Stein | | A61B 5/01 |
| 2019/0307430 A1 * | 10/2019 | Stein | | A61B 5/4306 |
| 2019/0343397 A1 * | 11/2019 | Meisal | | A61B 5/01 |
| 2019/0357891 A1 | 11/2019 | Pardey et al. | | |
| 2020/0000441 A1 * | 1/2020 | Lafon | | A61B 5/02438 |
| 2020/0113344 A1 * | 4/2020 | Youngblood | | A61B 5/11 |
| 2020/0178887 A1 * | 6/2020 | Correa Ramírez | | A61B 5/4809 |
| 2020/0394387 A1 * | 12/2020 | Chen | | G06V 40/20 |
| 2020/0405998 A1 * | 12/2020 | Franceschetti | | G16H 40/63 |
| 2021/0145415 A1 | 5/2021 | Lafon et al. | | |
| 2022/0000375 A1 * | 1/2022 | Meisal | | A61B 5/28 |
| 2022/0026284 A1 * | 1/2022 | Clements | | G01K 3/14 |
| 2022/0047250 A1 | 2/2022 | Clements et al. | | |
| 2022/0218314 A1 * | 7/2022 | Alexander | | A61B 5/7275 |
| 2022/0387003 A1 | 12/2022 | Zhang et al. | | |
| 2024/0074739 A1 | 3/2024 | Zhang et al. | | |

FOREIGN PATENT DOCUMENTS

| | | |
|---|---|---|
| CN | 109715074 | 5/2019 |
| CN | 111061944 | 4/2020 |
| EP | 3785641 | 3/2021 |
| JP | H08131408 | 5/1996 |
| JP | 2003164527 | 6/2003 |
| JP | 2006230790 | 9/2006 |
| JP | 2008264352 | 11/2008 |
| JP | 2010502338 | 1/2010 |

(56) References Cited

FOREIGN PATENT DOCUMENTS

| JP | 2014212977 | 11/2014 |
| JP | 2019051069 | 4/2019 |
| WO | WO 21/038025 | 3/2021 |

* cited by examiner

IN-BED TEMPERATURE ARRAY FOR MENSTRUAL CYCLE TRACKING

CROSS-REFERENCE TO RELATED APPLICATION

This application is a continuation of U.S. patent application Ser. No. 16/991,815, filed Aug. 12, 2020, the contents of which are incorporated herein by reference as if fully disclosed herein.

FIELD

The described embodiments relate generally to devices, methods, and systems for measuring a physiological parameter of a user. More particularly, the present embodiments relate to using temperature measurements to track the timing of a menstrual cycle.

BACKGROUND

A menstrual cycle starts with the first day of a period and ends when the next period begins. The first part of the cycle—pre-ovulation—prepares an egg to be released from an ovary and builds the lining of the uterus. Then, at ovulation, an egg is released from the ovary. The second part of the cycle prepares the uterus to accept a fertilized egg or to start a new cycle if pregnancy doesn't occur. A woman may be most likely to get pregnant during the two to three days before ovulation, and may desire to track their menstrual cycle for a variety of reasons including natural family planning.

An entire menstrual cycle typically lasts between 24 and 38 days, but the length may vary from cycle to cycle, and may also change over time (e.g., with age or changes in health). A woman may track her menstrual cycle using the basal body temperature (BBT) method, which typically includes the user measuring and recording her temperature every morning. An increase in temperature usually indicates that ovulation has occurred. Because the most fertile window occurs prior to ovulation, a user will typically track her menstrual cycle for multiple months to predict when she is likely to ovulate. The ovulation day may also be used predict the start date of the next menstrual cycle. However, variation in lengths of the cycle and subtle increases in temperature can make it difficult for some users to reliably predict the ovulation day.

SUMMARY

Embodiments described herein are directed to a method for tracking a menstrual cycle of a user. The method can include receiving temperature measurements from one or more temperature sensors in an array of temperature sensors positioned under the user on a bed an determining a use period for the array of temperature sensors when temperature measurements from at least one temperature sensor of the one or more temperature sensors exceeds a first temperature threshold for a duration. The method can also include identifying a set of temperatures that are within the use period and exceed a second temperature threshold, and, for each use period in a set of two or more use periods, determining a temperature of the user using the set of temperatures from the respective use period. The method can further include identifying at least one change in the temperature of the user between different use periods after determining the temperature of the user for each use period in the set of two or more use periods, and estimating an ovulation day of the user based on the at least one change in the temperature of the user.

In some cases, identifying the set of temperatures includes identifying temperatures from the use period that are below a third temperature threshold, determining the temperature of the user includes using temperatures from the set of temperatures that fall within a percentile range, and identifying the at least one change in the temperature of the user includes identifying that the temperature of the user increases by a shift threshold. In further examples, the second temperature threshold is greater than the first temperature threshold, the second temperature threshold is lower than typical body temperature, and the third temperature threshold is greater than typical body temperature. Predicting the ovulation day of the user can include determining at least two use periods in the set of two or more use periods where the temperature of the user is at least 0.1 degrees Celsius higher than two previous sleep periods in the set of two or more use periods. In other cases, predicting the ovulation day of the user includes determining at least one use period in the set of two or more use periods where the temperature of the user is at least 0.2 degrees Celsius higher than a maximum temperature of two previous sleep periods.

In some cases, the use period includes received temperature measurements from at least two temperature sensors of the array of temperature sensors, and the set of temperatures includes temperature measurements from the at least two temperature sensors. Determining the temperature of the user can include averaging the set of temperatures. Determining the temperature of the user can include determining an eighty-fifth percentile of the set of temperatures. In some examples, the duration is greater than 1 hour.

Embodiments are also directed to a system for tracking menstrual cycles that includes a strip configured to be positioned on a bed and an array of temperature sensors coupled to the strip and including first and second temperature sensors positioned at different locations on the strip. The system can also include a processor operative to receive temperature measurements from the first and second temperature sensors, detect a use period where received temperature measurements from at least one of the first or second temperature sensors exceed a first temperature threshold for a duration, and filter the received temperature measurements to identify a set of temperatures in the received temperature measurements from the use period that exceed a second temperature threshold. The processor can also be operative to determine a temperature of a user using the set of temperatures from the respective use period for each use period in a set of two or more use periods, identify at least one change in the temperature of the user between different use periods using the determined temperature for each use period, and estimate an ovulation day of the user based on the at least one change in the temperature of the user.

In some cases, the processor is operative to detect the use period where received temperature measurements from the first or second temperature sensors exceed the first temperature threshold for the duration and aggregate the received temperature measurements from the first and second temperature sensors for use sleep period. The array of temperature sensors can be positioned in a one-dimensional array across the strip. The first and second temperature sensors can be positioned between about 3 centimeters and about 6 centimeters apart. The strip can be configured to orient the array of temperature sensors across a width of the bed. In some cases, the array of temperature sensors includes one or more of a resistance temperature detector, a negative temperature coefficient detector, a thermocouple, a semiconductor temperature detector, or a combination thereof. The strip can include one or more position sensors that are operative to sense a location of the user, and detecting the use period for the first and second temperature sensors can be at least partially based on the sensed location of the user.

Embodiments described herein are also directed to a device for tracking a temperature of a user that includes a strip configured to be placed on a bed having a cover layer, a bottom layer, and a compliant layer positioned between the cover layer and the bottom layer. The device can also include an array of temperature sensors extending along a length of the strip and positioned between the cover layer and the bottom layer, and an interface device coupled to temperature sensors in the array of temperature sensors and configured to output a signal indicative of temperatures detected by the array of temperature sensors.

In some case, the strip comprises multiple stiffeners, each of the multiple stiffeners are positioned between the cover layer and a temperature sensor in the array of temperature sensors. A stiffener of the multiple stiffeners can be coupled to each temperature sensor, and the multiple stiffeners can each include a more rigid material than the cover layer. The strip can include a flexible layer positioned between the array of temperature sensors and the cover layer, and the flexible layer can extend along the length of the strip. The flexible layer can facilitate bending of the strip along the length. The interface device can be operative to receive temperature measurements from multiple temperature sensors in the array of temperature sensors, and the signal can include indications of temperatures measured by each of the multiple temperature sensors.

BRIEF DESCRIPTION OF THE DRAWINGS

The disclosure will be readily understood by the following detailed description in conjunction with the accompanying drawings, wherein like reference numerals designate like structural elements, and in which.

Figure 1:
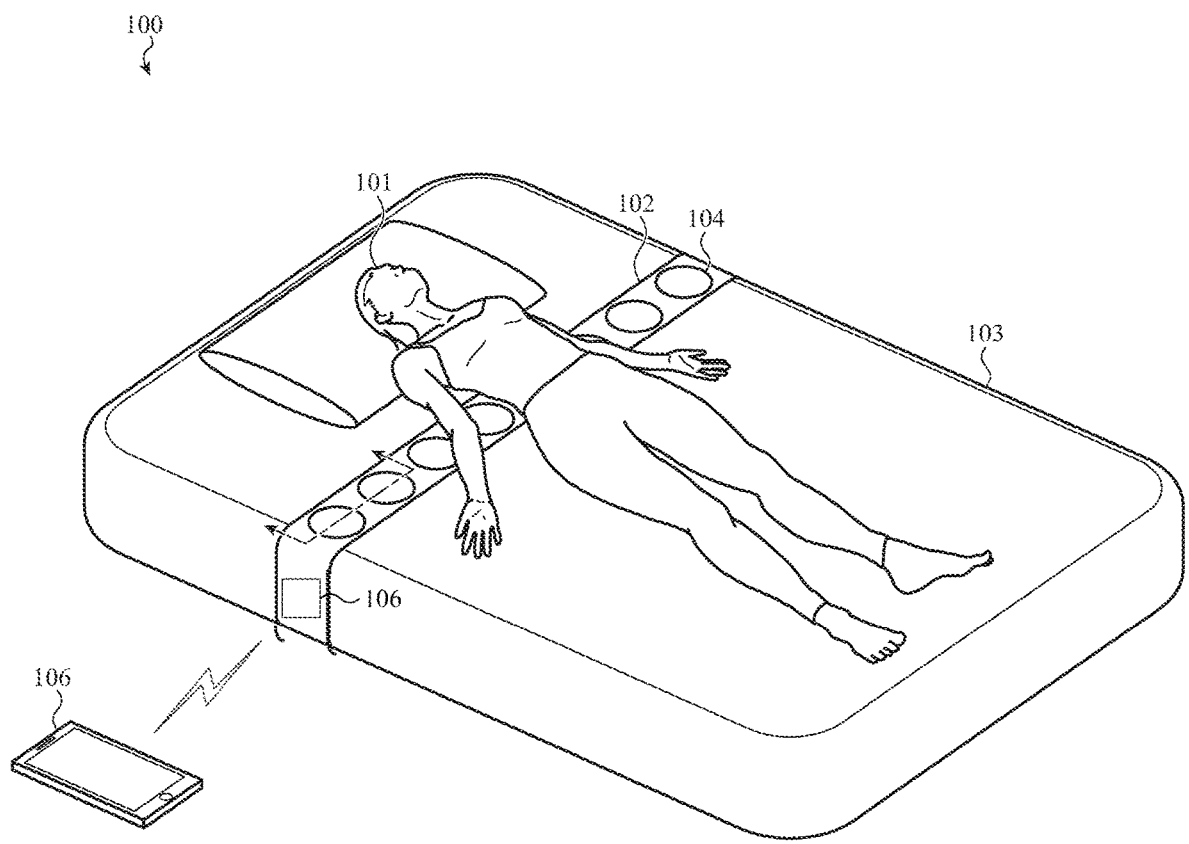
FIG. 1 shows an example temperature sensing system for menstrual cycle tracking.

It should be understood that the proportions and dimensions (either relative or absolute) of the various features and elements (and collections and groupings thereof) and the boundaries, separations, and positional relationships presented therebetween, are provided in the accompanying figures merely to facilitate an understanding of the various embodiments described herein and, accordingly, may not necessarily be presented or illustrated to scale, and are not intended to indicate any preference or requirement for an illustrated embodiment to the exclusion of embodiments described with reference thereto.

DETAILED DESCRIPTION

Reference will now be made in detail to representative embodiments illustrated in the accompanying drawings. It should be understood that the following description is not intended to limit the embodiments to one preferred embodiment. To the contrary, it is intended to cover alternatives, modifications, and equivalents as can be included within the spirit and scope of the described embodiments as defined by the appended claims.

Embodiments disclosed herein are directed to a temperature sensing system for menstrual cycle tracking. The temperature sensing system can be used to determine a basal body temperature (BBT) of a user while they are positioned in a bed. The BBT of the user can be tracked over multiple nights (sleep periods) and an increase in the BBT can be used to estimate an ovulation day. For example, if the nightly BBT of the user increases by a threshold amount, it can be estimated that ovulation occurred in the days immediately preceding the nightly BBT increase. This estimated ovulation day can be used to predict the start of a next period and/or the next ovulation day for a subsequent menstrual cycle.

The increase in temperature corresponding to the occurrence of ovulation can be subtle—on the order of 0.1 degrees Celsius—which can make it difficult to identify on which day ovulation occurred. For example, typical BBT techniques include a woman measuring her temperature upon waking up, but before getting out of bed. However, these typical techniques may not be precise enough to detect small changes in temperature (e.g., ~0.1 C changes) that can be associated with ovulation. Further, a single measurement point upon waking up can be associated with greater variation. As such, in some cases, typical BBT techniques may misidentify the ovulation day or only be able to narrow the ovulation day to a several day window. Further, the length of some women's menstrual periods and timing of ovulation during each menstrual period can change each menstrual period, which adds to uncertainty in identifying the ovulation day. As such, typical BBT techniques can result in high variability when predicting a next ovulation day for some women. For example, uncertainty in the ovulation day that arises from typical BBT tracking combined with non-regular cycle intervals can result in period start date and/or ovulation date predictions that vary by 10 or more days.

The temperature sensing system and techniques described herein may decrease the uncertainty in predicting a subsequent ovulation day by more accurately tracking changes in the BBT of a woman. These increased accuracy BBT changes can be used to improve the identification of ovulation timing, which can result in predicting a subsequent menstrual cycle start date and/or ovulation date with less uncertainty. In some cases, detecting and tracking BBT over an extended period of time, such as throughout the night, may help improve accuracy of the BBT as compared to traditional BBT measurement techniques that only rely on a single temperature measurement taken when the person awakes. Having multiple BBT data points over the extended period of time can allow the data to be processed and analyzed in a variety of ways that increases the accuracy of the determined BBT.

The temperature sensing system can include an array of temperature sensors that operate to measure a temperature of a user. In some embodiments, the array of temperature sensors can be configured in a flexible apparatus, such as a flexible mat, strip, or band that is positioned across or around a bed such that a user lying on the bed contacts one or more temperature sensors in the array. Temperature measurements from one or more of the sensors can be used to track the user's temperature as they sleep. The temperature measurements from one or more of these temperature sensors can be used to determine a BBT measurement for the user (e.g., a nightly BBT measurement). The temperature sensing system can track a user's BBT over multiple nights to identify small changes in temperature that are associated with ovulation, which small changes may not be detected using traditional BBT techniques. Further, in some cases, data from multiple sensors may be combined, compared, filtered, or otherwise analyzed to determine a nightly BBT measurement for the user. In some cases, the temperature sensing system can use multiple different temperature sensors to measure temperatures of a user as they move or otherwise change position throughout the night.

In some embodiments, temperature measurements from the array of temperature sensors can be used to identify which sensor a user is positioned over. For example, a use period can be detected for temperature sensors in the array. As used herein the term "use period" may refer to a time period that a user is in contact with one or more temperature sensor and temperature measurements from this period are used in determining a BBT for the user. For example, a use period can be nightly sleep period when a user is positioned over one or more temperature sensors. In some cases, detecting a use period can include determining whether a user was positioned over a temperature sensor for a sufficient amount of time to assume that temperature measurement from the sensor correspond to a BBT for the user. This can include determining whether temperature measurements from each temperature sensor exceed a first temperature threshold, which may be below body temperature but above typical room temperatures. Temperature sensors, which output temperature measurements above this first temperature threshold, may be determined to be in use such that it can assumed that a user is at least partially contacting these sensors and they are measuring a body temperature of the user. Temperature sensors, which output temperature measurements below this first temperature threshold, may be determined not to be in use such that their temperature measurements are not used in determining a body temperature of the user. Additionally, a duration of use for each temperature sensor can be determined. In some cases, only temperature sensors that output temperature measurements above the first temperature threshold (e.g., at or above 32 degrees Celsius) for a defined duration (e.g., 4 hours) are used to determine a BBT of the user. As used herein the term "use criteria" may refer to one or more parameters that are used to determine whether the user is positioned over a temperature sensor such that the temperature sensor can be considered to be in use. For example, the use criteria can include determining whether temperature measurements from each temperature sensor exceed a first temperature threshold for a defined duration. In this regard, the temperature data from sensors meeting the use criteria can be used in determining a BBT for the user. Temperature sensors that do not meet the use criteria may be assumed to not be positioned under a user, and the temperature data from these sensors may not be considered in determining the BBT for the user. The use criteria may be time dependent and different temperature sensors may meet the use criteria during different portions of a use period. Accordingly, a use period may include data from one or more temperature sensors that are determined to be located under a user.

In some cases, the array of temperature sensors may detect multiple different regions that meet the use criteria. These multiple regions can correspond to multiple people and or animals that are positioned in the bed and that meet these use criteria. In such cases, the temperature sensing system can uniquely identify different people and/or animals in the bed by comparing current temperature measurements to previous temperature data, a location of the user within the bed, detected sizes of the users, by one or more of the users identifying themselves through an app or other user interface, and so on.

In some cases, temperature measurements from sensors that meet the use and duration requirements can be further filtered to determine a nightly BBT for the user. For example, a temperature range that includes a second threshold temperature which is greater than the first threshold temperature and less than body temperature and a third threshold temperature which is greater than body temperature can be used to identify a set of temperatures from the temperature measurements meeting the use and duration criteria. This set of temperatures from one or more sensors in the array can then be used to determine a BBT of the user during a sleep period. In some cases, determining a BBT of the user for the sleep period can include performing one or more statistical analyses on the set of temperatures, such as averaging the set of temperatures, taking a percentile (e.g., eighty-fifth percentile), or a combination thereof. In some examples, determining a BBT of the user can include identifying thermal settling of temperature measurements for a user or a derivative of the thermal settling of the temperature measurements.

BBTs for a user can be determined for multiple sleep periods and compared to identify a change in the BBT that indicates ovulation has occurred. In some embodiments, detecting a shift in the temperature between two or more use periods can be used to identify an ovulation day. In some cases, an ovulation day can be determined when three consecutive days have a BBT that is 0.1 degrees Celsius higher than the previous six days. Additionally or alternatively, if one of three consecutive days has a BBT that is 0.2 degrees Celsius higher than the maximum of the previous six days, the day prior to the 0.2 degree Celsius increase can be estimated as the ovulation day. In some cases, determining the ovulation date can include evaluating the timing of a shift relative to the user's current day in their menstrual cycle, historical timing of the ovulation day for the user, the magnitude of the temperature shift compared to other temperature shifts in the cycle, or the like. In further embodiments this data or other tracked data, such as a period start date, typical menstrual phase lengths, and so on can be used to develop a statistical model, which can be used to determine if a temperature shift corresponds to an ovulation event.

The estimated ovulation day can be used to predict a subsequent ovulation day of the user. In some cases, the next period start date can be estimated as a defined number of days (or range of days) from the estimated ovulation day. In some cases, the number of days between the start of the period and the estimated ovulation day can be used to estimate the subsequent ovulation day. For example, if the temperature sensing system estimates for a first menstrual cycle that ovulation occurred 13 days after the start of the menstrual cycle, an ovulation day for a subsequent menstrual cycle can be predicted as occurring between 25-27 days (12-14 days until the start of the next menstrual cycle+13 days from the start of the menstrual cycle to ovulation) from the currently estimated ovulation day. This predicted ovulation day can be refined based on tracking one or more menstrual cycles for a user, which may decrease the uncertainty (range) of the predicted ovulation day. In some cases, the temperature sensing system can refine the estimate for when ovulation will occur in relation to the start of the menstrual cycle, which may be based on tracked data and/or statistical models that are developed for the user. Using these techniques, the temperature sensing system could estimate that ovulation may occur in shorter or longer period than 13 days after the start of the menstrual cycle. For example, the temperature sensing system could predict the next ovulation day as occurring 12, 14 or another number of days from the start of the menstrual cycle.

In some embodiments, the temperature sensing system can include a strip having temperature sensors positioned at defined intervals such that a user contacts multiple temperature sensors when they are laying on a bed. For example, the temperature sensing system may include a one-dimensional array of temperature sensors that are positioned between about 2 cm and about 8 cm apart. In some cases, the array of temperature sensors can include a two-dimensional array of sensors. The temperature sensors may be configured or positioned such that at least one temperature sensor is likely to be positioned under a central portion of the user's body. In some examples, temperature measurement from multiple temperature sensors may be compared to determine which sensors are located under a core portion of the user's body. In additional embodiments, the temperature sensing system can include other types of sensors that are used to determine one or more other physiological parameters of a user, such as position, heart rate, respiration, humidity, and so on. Outputs from these additional sensors may also be used to estimate an ovulation day of a user and/or predict a subsequent ovulation day.

These and other embodiments are discussed below with reference to FIGS. 1-6. However, those skilled in the art will readily appreciate that the detailed description given herein with respect to these figures is for explanatory purposes only and should not be construed as limiting.

FIG. 1 shows an example temperature sensing system 100 for menstrual cycle tracking. The temperature sensing system 100 can include a temperature sensing device 102 that is positioned on a bed 103. The temperature sensing device 102 can be configured as an array of temperature sensors that include multiple temperature sensors 104, and can be configured to be positioned on the bed 103 such that one or more temperature sensors 104 are located under a user 101 when the user is lying in the bed 103. The temperature sensing system 100 can also include a communications interface 106, an electronic device 108 that can receive temperature measurements from the temperature sensing device 102 and process the temperature measurements to determine one or more physiological parameters of a user, as described herein.

In some embodiments, the temperature sensing device 102 can include a flexible strip, mat, or band that is configured to be placed across a width of the bed 103. In some cases, the temperature sensing device 102 can be integrated into a bed sheet, blanket, the mattress, mattress pad or the like. In some examples, the temperature sensing device 102 can be integrated into other objects such as couches, chairs, rugs, or floors. In other cases, the temperature sensing device 102 could be worn or attached to the user such as being integrated into clothing, or other wearable items. The temperature sensing device 102 can be placed on the bed 103 such that one or more temperature sensors 104 are located under a core portion (e.g., a torso section) of the user 101. The temperature sensors 104 can be positioned along the strip, and spaced relative to each other, such that at least one temperature sensor 104 is likely to be completely positioned under the user 101. In other cases, the temperature sensors 104 can be positioned along the strip and spaced from each other such that multiple temperature sensors 104 are likely to be positioned under the user 101.

In some embodiments, the temperature sensing device 102 can include a one-dimensional array of temperature sensors as shown in FIG. 1, where multiple temperature sensors 104 are arranged in a single line. In other cases, the temperature sensing device 102 can include a two-dimensional array of temperature sensors, where multiple temperature sensors 104 extend in at least two directions. The two-dimensional array can include temperature sensors 104 that are positioned in a variety of configurations such as square, rectangular, circular, or to correspond to the shape of a user. For example, the temperature sensing device 102 can be configured to correspond to the shape of a torso section of the user 101 when the user 101 is laying on their back, side, or front. In this regard, the location of temperature sensors 104 relative to a user 101 may be assumed based on their location within the array and/or based on temperature outputs from each temperature sensor 104. For example, if the user 101 is lying on their back over the temperature sensing device 102, temperature measurements from each temperature sensor 104 can be compared to determine a user's position relative to the temperature sensing device 102. Further, in some cases, this comparison may be used to determine a location of specific temperature sensors 104 relative to the user 101, for example, that a temperature sensor 104 located centrally within the array of temperature sensors 104 is located under or near the spine of the user 101. Regardless of whether the temperature sensing device 102 is configured with a one-dimensional array, two-dimensional array, or other configuration of temperature sensors, the temperature sensing device 102 may be positioned on, or integrated into, the top surface of the bed 103.

In some cases, the size of the temperature sensing device 102 can be configured to accommodate different numbers of people lying on a bed and/or different sized beds. The temperature sensing device 102 may be wide enough to accommodate a single user, such that at least one or more temperature sensors 104 are positioned under the user 101 as he or she lays on the bed. In some examples, the temperature sensing device 102 can be configured to extend across a width of the bed, such that temperature sensors 104 span the entire width of the bed. In other cases, the temperature sensing device 102 can be configured to distinguish one user from another user and/or operate the temperature sensors in different sets for different users.

The temperature sensors 104 can be configured to detect a temperature of the user 101 and/or surrounding environment and output a signal indicative of the detected temperature. In some cases, each temperature sensor 104 outputs a signal to the communications interface 106 that indicates a measured temperature and uniquely identifies the temperature sensor 104 and/or a position of the temperature sensor in the temperature sensing device 102. For example, a first temperature sensor 104a can output a temperature measurement signal along with a unique identifier that indicates that it is the third temperature sensor 104 in the array. Similarly, a second temperature sensor 104b can output a temperature measurement signal along with a unique identifier that indicates that it is the seventh temperature sensor 104 in the array. Accordingly, the temperature sensing device 102 can output multiple temperature measurements that correspond to different temperature sensors 104 within the array. In some cases, the temperature sensing device 102 can output multiple temperature sensor signals and each signal corresponds to a different temperature sensor 104. In other cases, the array can output a single analog or digital signal that contains temperature measurements for each temperature sensor 104 in the array. For example, temperature measurements for all of the temperature sensors 104 can be read out in a predetermined sequence, with positions in the sequence identifying particular temperature sensors 104 and/or their positions within the temperature sensing device 102.

The temperature sensing device 102 can also include communications interface 106 that is configured to collect outputs from the temperature sensors 104 and communicate them to one or more peripheral devices for processing and/or displaying temperature data to the user 101. The communications interface 106 can include a processor or controller for acquiring temperature signals from the temperature sensors 104, which can be analog or digital signals. The communications interface 106 can process, analyze and/or digitize the temperature signals before transmitting them to one or more peripheral device such as the electronic device 108. In some cases, this includes filtering the temperature signals, associating temperature data with a time stamp, identifying which temperature sensor 104 each temperature signal corresponds to, and so on. In some cases, the communications interface 106 can include a power source such as a battery and/or plug in power source.

The electronic device 108 can be a standalone device such as a smartphone, a tablet, a laptop, a computer, a virtual assistant, a wearable device such as a watch, a wristband, or a physiological monitoring device, or other electronic device. In some cases, the electronic device 108 can be integrated into the temperature sensing device 102, for example, the electronic device 108 can include a user interface that is integrated with the communications interface 106. The electronic device 108 can communicate with the temperature sensing device 102 (e.g., communications interface 106) using wired or wireless connections. The electronic device 108 can be configured to receive temperature measurements from the temperature sensing device 102, analyze and/or process the temperature data, and output information to a user. For example, the electronic device 108 can be configured to determine a temperature for each use period of a user 101 and identify an increase in the temperature of the user 101, which is associated with a menstrual cycle event such as ovulation, as described herein. The electronic device 108 can use this temperature information in a variety of ways such as estimating a day that ovulation occurred from temperature changes of a user, predicting a start date of a next menstrual cycle, predicating an ovulation date in a subsequent menstrual cycle, and so on.

In some cases, the electronic device 108 can track temperature information of the user 101 to identify fevers, illness, or other events associated with other cycles, conditions, ailments, or diseases. In some examples, the electronic device 108 can use the temperature data when evaluating a sleep quality of the user 101. In other cases, the temperature sensing device 102 can be used to detect the presence of the user 101 in the bed. For example, an increase in temperature detected by one or more sensors in the array could be used to determine that a user is positioned in the bed above one or more of the temperature sensors.

In some embodiments, the temperature sensing system 100 can include additional sensors and/or receive data from other external sensors that can be used in conjunction with the temperature sensors to track menstrual cycles of the user 101. For example, the temperature sensing device 102 can include touch, force, or pressure sensors that identify a position of the user relative to the array of temperature sensors 104. Such position data can be used to identify temperature sensors that are positioned under the user 101, such that temperature measurements from these sensors can be used while temperature measurements from other sensors that are not positioned under the user 101 can be discarded or ignored. In some cases, outputs from touch, force, and/or pressure sensors could be used to determine if a user is contacting a specific temperature sensor 104 or a degree of contact with a specific temperature sensor 104. In further examples, the temperature sensing system 100 can include one or more sensors to track heart rate, respiration, blood pressure, humidity data, body weight, or other physiological parameters associated with the user 101.

In some cases, the temperature sensors 104 can be used to determine a position of the user 101 on the bed 103 and/or relative to the temperature sensing device 102. For example, temperature data from the temperature sensors 104 can be used to determine where the user 101 is positioned on the temperature sensing device 102. In some cases, temperature data from the temperature sensors 104 can be used to determine a posture of the user 101 in the bed 103, such as whether the user 101 is laying on their back, side, or stomach.

In some cases, one or more position sensors can be used to sense a location of the user on the bed and/or relative to temperature sensors in the array. Position sensor data can be used to determine the use period for the first and second temperature sensors. For example, if the position sensors detect that the user is positioned over the first and second temperature sensors for the defined duration, this location data could be used in determining the use period for the array of temperature sensors.

Additionally or alternatively, the temperature sensing device and or one or more other sensors such as position sensors can be used to determine whether multiple people and/or animals are located in the bed 103. For example, the temperature data from the temperature sensors 104 can be analyzed to determine if there are more than one increased thermal regions which can indicate multiple bodies are on the bed 103. The temperature data can be analyzed along with other sensor data such as position sensor data.

The temperature sensing system 100 can be implemented in a variety of ways. For example, in addition or alternatively to the bed sensor described herein, the temperature sensing system 100 can be implemented in wearable devices such as a smart watch, a wearable health tracking monitor, in clothing worn by the user, head bands, glasses, or a combination thereof. Data from these devices can be used individually or in conjunction with the bed-based sensor for tracking menstrual cycles of a user as described herein.

Figure 2:
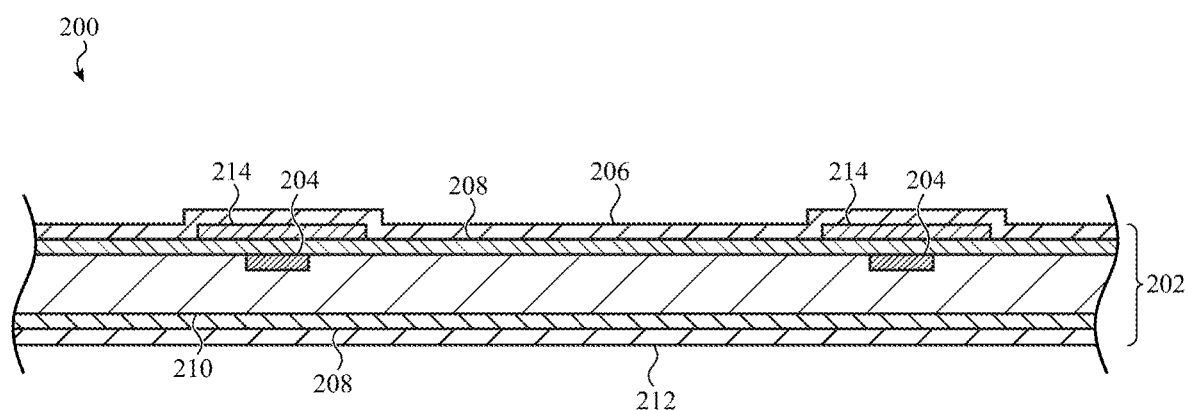
FIG. 2 shows a cross-sectional view of an example temperature sensing device for menstrual cycle tracking.

FIG. 2 shows a cross-sectional view of an example of a temperature sensing device 200 that can be used for menstrual cycle tracking. The cross-section is taken along section line A-A in FIG. 1. The temperature sensing device 200 is an example of the temperature sensing devices described herein, such as the temperature sensing device 102. The temperature sensing device 200 can include a sensor stack 202 that contains one or more temperature sensors 204. The temperature sensing device 200 can be configured as an array of temperature sensors 204 that are operative to be positioned on a bed, worn by a user, or otherwise configured to be positioned under a user as described herein.

In some embodiments, the sensor stack 202 can include one or more layers that contain the temperature sensors 204. For example, the sensor stack 202 can include a cover layer 206 formed from a first material, which forms a top layer of the temperature sensing device 200. The cover layer 206, alone or in combination with other layers or components, can seal the temperature sensors 204 from the surrounding environment to protect them from physical damage, moisture, or other environment factors. In some cases, the cover layer 206 can be formed from a flexible material and configured to transfer heat from a user to the temperature sensors 204. For example, the cover layer 206 may be relatively thin to decrease its resistance to heat transfer from the user and to the temperature sensors 204. The sensor stack 202 can also include one or more flexible layers 208. The flexible layers 208 can be coupled with the temperature sensors 204 and allow the sensor stack 202 to bend, flex, or otherwise deform, to allow the temperature sensors 204 to move relative to each other. In some cases, the sensor stack 202 can also include a compliant middle layer 210, which can compress, bend, twist, expand, or otherwise deform to help the sensor stack 202 conform to the body of a user. In additional examples, the sensor stack 202 can include a bottom layer 212, which can be configured to couple the temperature sensing device 200 with a bed. For example the bottom layer 212 can be formed from a high friction material, an adhesive material, a hook-and-loop fastener, or any other suitable material that can removably couple the temperature sensing device 200 to a bed. In this regard, the temperature sensing device 200 can be removed and reattached to the bed. The layer of the sensor stack 202 can form a flexible array that can be positioned on a bed or other surface and conform to the unique contours of an individual user such as the shape of a user's back, side, or front as they lay on the bed. In some cases, the temperature sensing device 200 can be configured to attach to other objects such as clothing, headbands, wristbands, chairs, and so on.

In some embodiments, the temperature sensing device 200 can include one or more stiffeners 214 that are positioned between the temperature sensors 204 and the cover layer 206. The stiffeners 214 can protect the temperature sensors 204 from mechanical damage such as detachment of electrical contacts when the sensor stack 202 flexes to conform to the shape of a user. The stiffeners 214 can also aid heat transfer between a user and the temperature sensors 204, and/or help develop a stable reading of a body temperature of a user.

Temperature sensors 204 can include one or more of resistance temperature detectors (RTD), negative temperature coefficient (NTC) detectors, thermocouples, semiconductor temperature detectors, or any other suitable temperature detectors, or any combination thereof. In some cases, the temperature sensors 204 can be configured as single heat flux temperature sensors and/or dual heat flux temperature sensors such as four-point temperature sensors that can be operated to estimate a subsurface temperature of a user.

Figure 3:
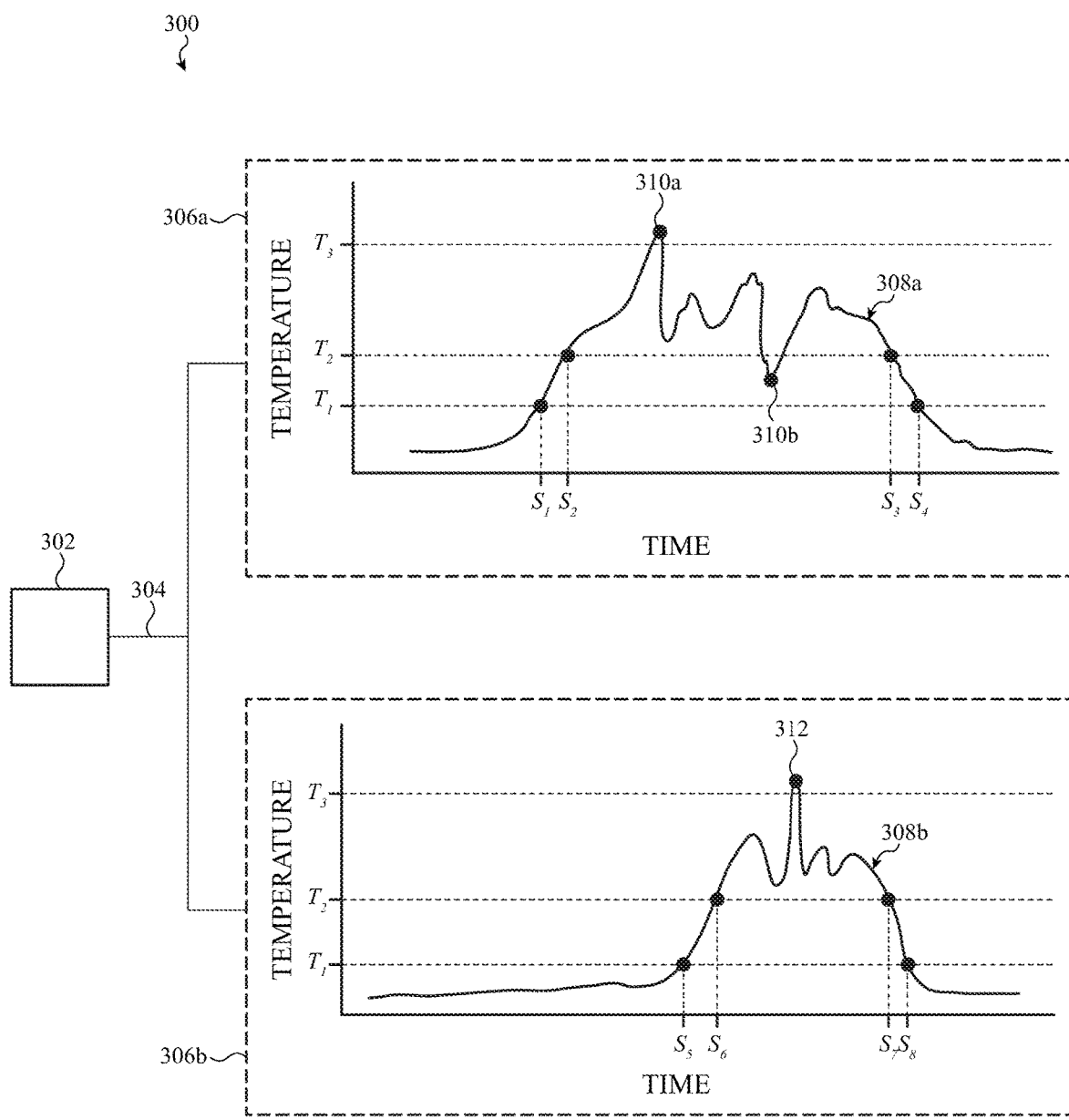
FIG. 3 shows an example output from a temperature sensing device that is used for menstrual cycle tracking.

FIG. 3 shows an example output 300 from a temperature sensing device 302 that is used for menstrual cycle tracking. The example shown in FIG. 3 includes a temperature sensing device 302, which may be an example of the temperature sensing devices described herein (e.g., temperature sensing devices 102 and 200). The temperature sensing device 302 can output a temperature signal 304 that includes temperature measurements 306 from one or more temperature sensors, which may be examples of the temperature sensors described herein (e.g., temperature sensors 104, 204). The temperature measurements 306 can include temperature measurements associated with each temperature sensor in the temperature sensing device 302.

Temperature measurements from the temperature sensing device 302 can be analyzed and processed to determine a temperature of a user during a use period of the array of temperature sensors. The use period can be used to a continuous duration of time when the user is positioned over at least one temperature sensor of the array of temperature sensors. The duration can be selected to such that it can be assumed that the user was at rest and their temperature during the use period represents their BBT. In some cases, the use period can be have a duration that extends over a portion of or a substantial entirety of a rest period of a user such as period where the user is sleeping. Accordingly, the temperature measurements falling within this use period can be analyzed over a longer time period which may increase the accuracy of the user's temperature. For example, a longer user period may allow temperature measurements for one or more temperature sensors falling within this duration to be filtered, averaged, or otherwise analyzed to improve the accuracy of the determined temperature for the user. In some cases, the use period can include a period in which the user is positioned over more than one temperature sensor, and thus, the use period can include a duration that the user was positioned over a first temperature sensors and a duration that the user was positioned over a second temperature sensor, which may or may not overlap in time.

Determining a use period for the array of temperature sensors can include evaluating each temperature sensor in the temperature sensing device to determine whether it was positioned under and/or contacting the user. A use period can be a period of time in which one or more temperature sensors output temperature measurements that are above a first temperature threshold (e.g., T1, shown in FIG. 3) for a defined duration. The use period can be used to identify a period of time in which a user is positioned above one or more temperature sensor such that temperature measurements from the respective temperature sensors correspond to a BBT of the user. For example, the duration in which the user is positioned above one or more temperature sensors, can be set to a length of time that corresponds to a sleep period of a user. Thus, the use period can occur while a user is sleeping in their bed.

Temperature measurements from each temperature sensor can be analyzed to determine how long the user was positioned above a respective temperature sensor. Temperature measurements from temperature sensors that are positioned under a user for a defined duration may be considered in the temperature analysis. For example, temperature sensors that output temperature measurements that are above a first temperature threshold (T1) for the defined duration will be considered within the use period.

FIG. 3 illustrates first temperature measurements 306a that are associated with a first temperature sensor, and second temperature measurements 306b that are associated with a second temperature sensor. Two temperature measurements 306 are shown for clarity, however the temperature sensing device 302 could include more or less temperature measurements based on the number of active temperature sensors in the array. Temperature measurements 306 from one or more temperature sensors can be used to determine a use period for the array of temperature sensors.

The first temperature measurements 306a, output by the first temperature senor, may be analyzed, for example by the electronic device as described herein, to identify and/or isolate one or more portions of the first temperature measurements 306a (e.g., a set of temperature measurements) that will be used to determine a temperature of the user. In the example shown in FIG. 3, the first temperature measurements 306a are above the first temperature threshold (T1) for a first duration that includes the time period between a first time (S1) and a fourth time (S4). The first temperature measurements 306a can include a series of first temperature values 308a taken over the first duration. If this first duration is longer than a defined duration for the user period (e.g., minimum use duration), then the first temperature values 308a occurring within the first duration can be used to define the use period, which would occur from the first time (S1) to the fourth time (S4).

The second temperature measurements 306b are above the first temperature threshold (T1) for a second duration that includes the time period between a fifth time (S5) and an eighth time (S8). If this second duration is longer than the defined duration for the use period (e.g., minimum use duration), then the second temperature values 308a occurring within the second duration can also be used to define the use period. In some cases, the use period can include overlapping times. For example, the first duration between the first time (S1) and the fourth time (S4) and the second duration between the fifth time (S5) and the eighth time (S8), which occurs within the first duration. In other examples, the use period could include a longer period in which temperature measurements from one sensor satisfying the defined duration partially overlap with temperature measurements from another sensor that also satisfies the defined duration. In this regard, the use period could be longer than the period of time in which any individual sensor is above the first temperature threshold for the defined duration. In further examples, the use period can include non-overlapping temperature measurements from different temperature sensors. For example, a first duration where a first temperature sensors is above the first temperature threshold (T1) for the defined duration, followed by a period of time where none of the temperature sensors are above the first temperature threshold (T1), followed by a second duration in which the another temperature sensor is above the first temperate threshold (T1) for the defined duration. This may occur if a user sleeps in a first position and then moves and sleeps in a second position.

The analysis can include determining whether a user was positioned over the first temperature sensor and/or the second temperature sensor during the sleep period, which can be used to decide whether temperature measurements from these sensors will be considered for determining a user temperature for that sleep period. For example, temperature values 308 from the first sleep period (S1-S5) can be compared to a first temperature threshold (T1), and if the temperature values 308 are above the first temperature threshold, then they system can determine that the temperature sensor was in positioned under or in contact with the user during the sleep period. In some cases, the first temperature threshold may be above typical room temperatures, but below typical body temperatures. For example, the first temperature threshold (T1) can be in the range of 22 degrees Celsius to 34 degrees Celsius. In some cases, the first temperature threshold can be set to about 32 degrees Celsius.

In the example of FIG. 3, the first temperature values 308a that span a first duration occurring between the first time (S1) and the fourth time (S4) are above the first temperature threshold (T1), and the second temperature values 308b that span a second duration occurring between a fifth time (S5) and an eighth time (S8) are above the first temperature threshold (T1). For the sake of illustration, both the first and second durations are considered to be longer than the defined duration for the user period. The use period can include the period of time between the first time (S1) and the fourth time (S4) and the period of time between the fifth time (S5) and the eighth time (S8), which can be overlapping. Accordingly, first temperature values 308a between the second time (S2) to the fourth time (S4), and second temperature values from the sixth time (S6) to the eighth time (S8) may be further analyzed to determine a temperature of a user during the use period.

Temperature sensors that output temperature measurements below the first threshold (T1) may be considered to be inactive during the sleep period and may not be used in determining a temperature of the user for that sleep period.

In some embodiments, temperature values 308 measured during the use period can be further processed to filter out temperature measurements that deviate from typical body temperature. Typical body temperature can be considered to be between about 36.5 degrees Celsius and 37.5 degrees Celsius. The first temperature values 308a that occur between the first time (S2) and the fourth time (S4) and the second temperature values 308b that occur between the fifth time (S5) and the eight time (S8) can be filtered to remove values within that duration that fall outside a defined temperature range. In some cases, the temperature range can be defined by a second temperature threshold (T2) that is greater than the first temperature threshold (T1) and below typical body temperature. For example, the second temperature threshold (T2) can be set to 34 degrees Celsius. Temperature values 308 below the second temperature threshold (T2) can be removed from the BBT analysis. Additionally or alternatively, the temperature range can be further defined by a third temperature threshold (T3) that is greater than the second temperature threshold (T2) and also greater than standard body temperatures of a human. For example, the third temperature threshold (T3) can be set to 38 degrees Celsius. Temperature values 308 above the third temperature threshold (T3) can be removed from the BBT analysis. The remaining temperature values 308 can define a set of temperatures that are used to determine the temperature of the user for the sleep period.

In the example of FIG. 3, the set of temperatures that is used to determine the temperature of the user for the use period can include the first temperature values 308a that were measured during the time duration from a second time (S2) to a third time (S3). In some cases, outlying first temperature values 308a such as a first outlying value 310a, and a second outlying value 310b that are within the time duration from the second time (S2) to the third time (S3) can be filtered or otherwise removed from the set of temperatures. The set of temperatures can also include the second temperature values 308b that were measured during the time duration from a sixth time (S6) to a seventh time (S7). In some cases, outlying second temperature values 308b such as a first outlying value 312 that are within the time duration from the sixth time (S6) to the seventh time (S7) can also be filtered or otherwise removed from the set of temperatures.

An analysis including evaluating the use criteria, a duration parameter, and filtering the temperature measurements to identify a set of temperatures that is used in determining a temperature of a user can be performed for each sleep period. Accordingly, the system can output a temperature of the user for each use period in a series of use periods, such as multiple nights of sleep. The use criteria, duration parameter, and filtering may result in more accurate BBT measurements by using temperature values that are taken during an extended rest period of the user, and removing temperature variations that may be due to non-user factors such as a heater warming a temperature sensor, an electronic device being left in the bed and causing inaccurate temperature measurements, movement of the user that results in contact with different temperature sensors, and so on.

In some cases, the set of temperatures can be analyzed in various ways to determine a temperature of the user for the use period. For example, a percentile of the set of temperatures can be calculated and used to determine the temperature of the user. In some examples, an eighty-fifth percentile for the set of temperatures may be used to determine the temperature of the user for the use period. In other examples, the set of temperatures can be averaged or processed using other statistical analysis to determine the temperature of the user for the use period.

In some embodiments, machine learning can be used to determine the temperature of the user. For example, one or more machine learning models can be configured to, or trained to, evaluate the temperature measurements from a use period to determine a temperature of the user during the use period. Additionally or alternatively, the one or more machine learning models can be configured to, or trained to, identify, label, and/or classify temperature variations between different use periods to identify a temperature shift associated with ovulation of the user. In some cases, the machine learning model can be trained to recognize specific types of temperature shifts or patterns associated with temperature variations that are indicative of ovulation. The machine learning models can be configured to monitor changes in a specific user's temperature over time to identify and or classify temperature shifts that are associated with ovulation or other phases in the menstrual cycle such as the start of a user's period.

The determined temperature can be displayed or otherwise reported to the user as their BTT for the use period. For example, the determined temperature determined that results from aggregating and analyzing the temperature sensor data for a use period, such as a nightly BBT, can be displayed to the user as a single value. Additionally or alternatively, temperature measurements from each temperature sensor can be logged and/or viewed by the user. In this way, a user's temperature variability or other temperature trends can be view by the user and/or further analyzed.

Figure 4:
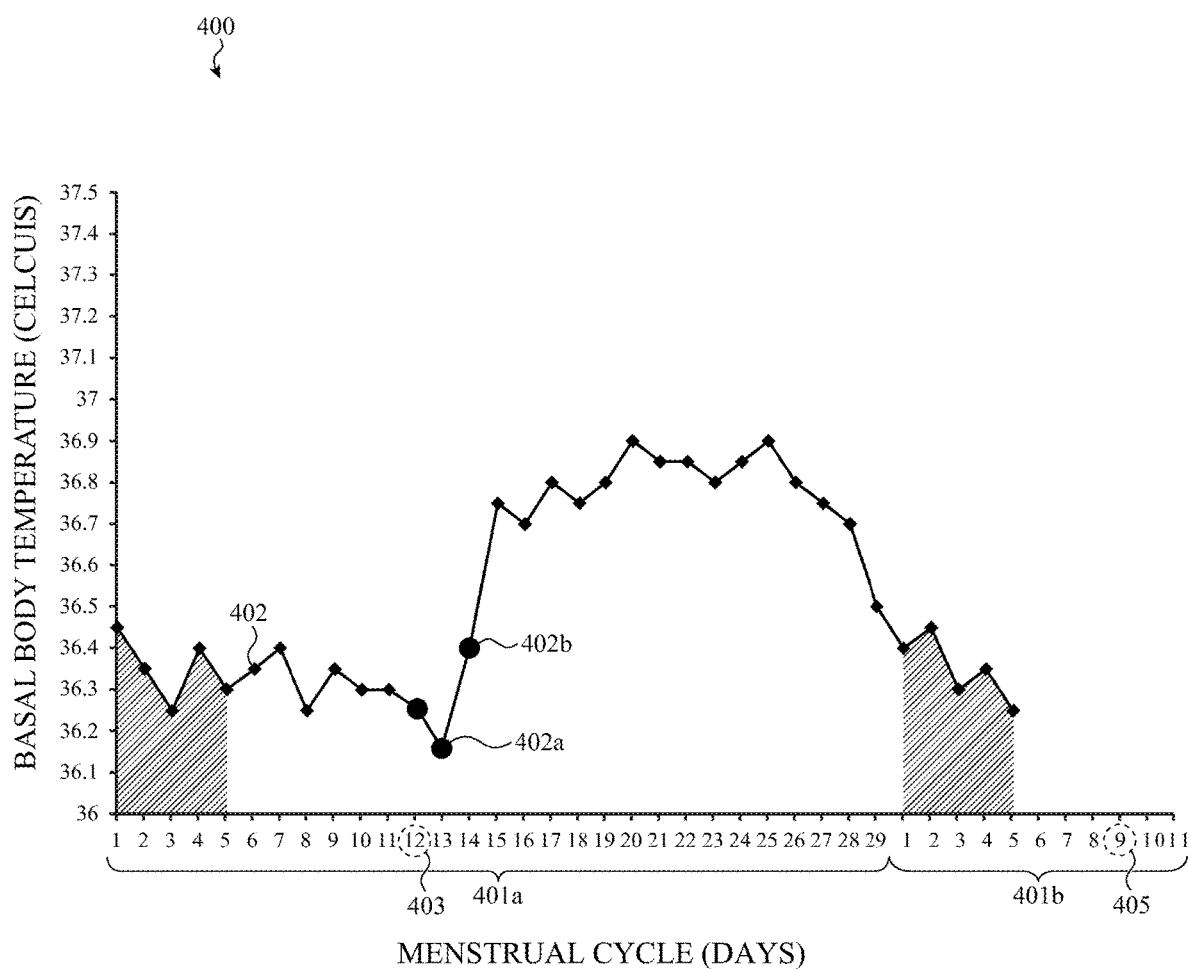
FIG. 4 shows an example analysis that may be performed by a temperature sensing system for menstrual cycle tracking.

FIG. 4 shows an example analysis 400 that may be performed by a temperature sensing system for menstrual cycle tracking. The analysis 400 can include tracking temperatures 402 of a user for multiple use periods to identify changes in the temperature 402 of a user between different use periods. The temperatures 402 can be determined using a temperature sensing system such as one of the temperature sensing systems described herein (e.g., temperature sensing system 100), which include a temperature sensing device that outputs temperature measurements from one or more temperature sensors such as the temperature sensing devices described herein (e.g., temperature sensing devices 102, 200, and 302). The temperatures 402 can be determined using one of the techniques described herein, such as by analyzing use criteria, evaluating duration parameters, and filtering temperature data as described herein, for example with reference to FIGS. 1-3.

In some embodiments, the temperatures 402 can be used to identify different phases that occur within a menstrual cycle 401. Each menstrual cycle 401 starts on the day the period begins and ends when the next period begins. Temperatures 402 during each menstrual cycle 401 typically exhibit a biphasic pattern, where they are lower prior to ovulation and higher after ovulation. An increase in BBT during a menstrual cycle may be referred to as a "temperature shift." However, in some cases a user may have an increase in temperature ("shift") that is a result of other factors such as fever, environment, and so on. Determining when the temperature increase occurred (or is occurring) can be used to estimate an ovulation day 403 for a current menstrual cycle 401a. For example, the temperature sensing system can be configured to identify temperature changes between use periods, which can include identifying an increase or decrease in temperature (temperature shift) from a first night to a second night. After identifying one or more temperature increases or decreases (shifts), the temperature sensing system can determine if a temperature shift corresponds to an ovulation day. In the cases where multiple temperature shifts are detected, the temperature sensing system can identify which temperature shift corresponds to the ovulation day. This can include evaluating the timing of the temperature shift relative to when it occurred within the ovulation cycle, the historical timing of ovulation for the user, a magnitude of the shift compared to other temperature shifts, and so on. In some cases, information inputted by a user such as a period start date also may be used. This information can be used to generate a statistical model for the user, which can be used to determine if a detected temperature shift corresponds to ovulation or some other event.

In some embodiments, the ovulation day 403 can be estimated by determining when the temperature 402 between two use periods increases by a defined threshold. For example, if the difference between a first temperature 402a from a first use period and a second temperature 402b from a second use period increases more than the defined threshold, then the day of the first use period 402a may be estimated as the ovulation day 403.

In some embodiments, additional temperatures 402 may be used to estimate the ovulation day 403. For example, the ovulation day 403 may be estimated by determining two or more consecutive days that have temperatures 402 that are a defined threshold higher than at least the two previous days. For example, the ovulation day 403 can be estimated as the day when the next three days have temperatures 402 that are 0.1 degrees Celsius higher than the previous six days. In other examples, the ovulation day 403 can be estimated as the day when the next three days have temperatures 402 that are 0.2 degrees Celsius higher than the maximum of the previous six days. In further examples, the ovulation day 403 can be estimated as the day when the temperature 402 of the user is at least 0.2 degrees Celsius higher than a maximum temperature of two previous sleep periods.

In some cases, the estimated ovulation day 403 determined for a current menstrual cycle 401a can be used to predict the start day of a subsequent menstrual cycle 401b and/or a subsequent ovulation day 405 for the subsequent menstrual cycle 401b. In some cases, menstrual cycle start dates and/or ovulation can be tracked over multiple menstrual cycles 401, and this combined data can be used to predict menstrual events such as a period start day, an ovulation day, and so on for subsequent menstrual cycles 401.

In some cases, the next period 401b start date can be predicted as being a defined number of days from the estimated ovulation day 403. In further examples, the next ovulation day 405 can be predicted as being a defined number of days from the estimated ovulation day 403 and/or a defined number of days from the next period start day. In some cases, the next period 401b start date can be entered by the user, for example, the user may indicate the day that their period started using a user interface of an electronic device, such as the electronic device described herein. In further examples, the defined number of days used to predict the next period 401b start date and/or the next ovulation day 405 can be based on data that was tracked from previous menstrual cycles 401a. In some cases, predicted period start days, and/or predicted ovulation days may be presented as a range of days that these events are likely to occur. For example, an estimated ovulation day 403 for the current menstrual cycle 401a can be estimated using multiple different methods as described herein. Then, based on each of these methods and uncertainty due to cycle to cycle variations, the predicted ovulation day 405 for a subsequent cycle 401b can be presented as a range of days that ovulation is most likely to occur. For example, the predicated ovulation day 405 can be predicted to be a three day range that could occur between days eight, nine and ten in the next period 401b.

In some embodiments, a user may enter information that is used to predict the next menstrual cycle 401b start date, ovulation day 405, and so on. For example, the user may enter a day when her period started, her age, body mass index, or other metrics that may be used to refine the start dates. For example, a user may enter data related to the intake of food, alcohol, medications, and so on. In some cases, the temperature sensing system can receive inputs from other sensors such as heart rate information, heart rate variability, respiration, blood pressure, and the like, which may be used to predict the next period start date 401b, a next ovulation day 405, and so on. Additionally or alternatively, other factors may be used to predict menstrual cycle timing of a user such as time the user falls asleep and/or wakes each day, which may be detected by one or more sensors or entered by the user.

Figure 5:
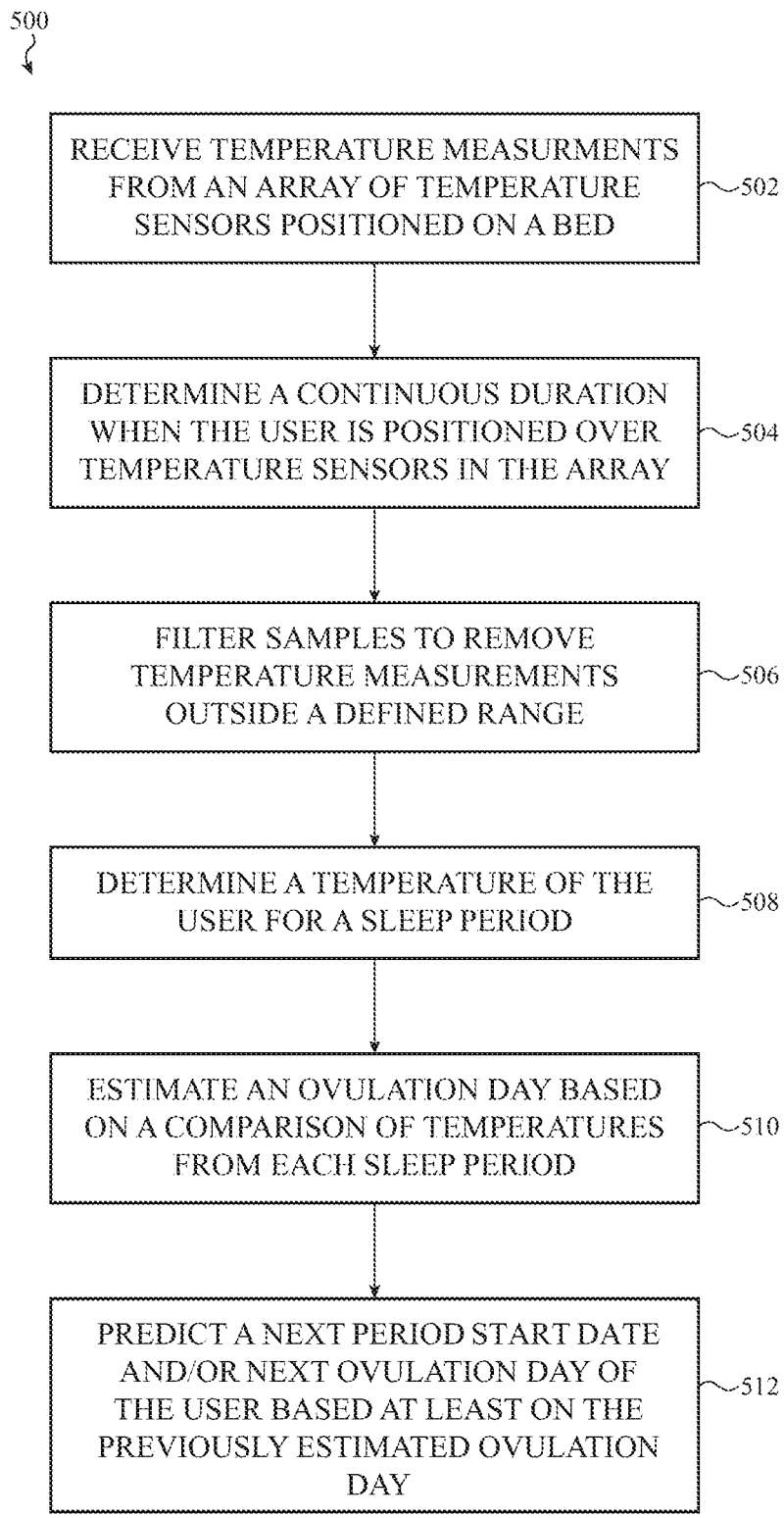
FIG. 5 shows an example method of operating a temperature sensing system for menstrual cycle tracking.

FIG. 5 shows an example method 500 of operating a temperature sensing system for menstrual cycle tracking. The temperature sensing system can be an example of the temperature sensing systems described herein such as temperature sensing system 100.

At 502, the method 500 can include receiving temperature measurements from an array of temperature sensors positioned on a bed. The array of temperature sensors can be part of a temperature sensing device described herein. In some cases, the array of temperature sensors can be a one-dimensional array that is configured to extend across a mattress of a bed. In some cases, the temperature sensing device can extend around one or more portions of the mattress to secure the temperature array to the bed. Temperature sensors of the array can be located on a top surface of the mattress while other portions of the device wrap around the mattress. In some cases, the array of temperature sensors can include one or more temperature sensors that would be located outside a sleeping area of a user such as on the side of the mattress. Such sensor(s) can be used to measure environmental temperatures, which can be used to compare to measured temperatures of a user. For example, environmental temperatures could be used to calibrate other sensors, set one or more temperature thresholds such as the first, second or third temperature thresholds described herein, or the like.

At 504, the method 500 can include determining a continuous duration when the user is positioned over temperature sensors in the array. In some cases, this includes determining a use period for the temperature array when temperature measurements from one or more temperature sensors in the array exceed a first temperature threshold for a duration. This can be based on a single temperature sensor exceeding the first temperature threshold temperature for a continuous duration, an average temperature exceeding the first temperature threshold for the duration, at least one temperature sensors (but maybe different ones) combining to exceed the first temperature threshold for the duration, or an average temperature of two or more sensors exceeding the first temperature threshold for the duration, and so on.

In some examples, the temperature sensing system can include other sensors such as touch or force sensors that are used to determine a location of the user relative to the array of temperature sensors. Such touch data can be used to determine which sensors are in use and/or combined with temperature data to determine if the user is positioned over temperature sensors in the array. In further examples, other sensors can be used to determine whether a user is positioned over the array of temperature sensors, for example, light sensors, humidity sensors, physiological sensors, such as a heart rate monitor, and so on, could be implemented as part of the temperature sensing system.

At 506, the method 500 can include filtering samples to remove temperature measurements outside a defined range. The filtering can include removing temperature measurements that deviate from typical body temperature, which can be due to a measurement artifact or other event. The filter can include identifying a set of temperatures that are within the use period and exceed a second temperature threshold. For example, identifying the set of temperatures can include defining a temperature range and temperature measurements falling outside this range and removing or ignoring temperature values falling outside this range from the BTT analysis. The temperature range can include a lower bound that is between room temperature and body temperature and an upper bound that is slightly above body temperature. In some cases, the lower temperature bound can be set above the first temperature threshold that is used to determine the continuous use duration of the device as described herein. For example, the lower temperature bound can be between 24 and 34 degrees Celsius, and the upper temperature bound can be above 37 degrees Celsius. In some cases, the temperature range can be between 34 degrees Celsius and 38 degrees Celsius.

At 508, the method 500 can include determining a temperature of the user for a use period. This can include using temperature measurements from the use period and that were filtered as described herein. In some cases, temperature measurements for a user are determined for multiple use periods. This can include determining a set of temperatures for each use period such as by filtering temperature measurements that occur within the use period. Temperature measurements for a user can be determined for multiple consecutive use periods such as a set of two or more use periods. In this regard, temperature changes that occur between use periods can be tracked over time. For example, the determined temperatures for each use period can correspond to a nightly BBT temperature of a user. Accordingly, temperatures of the user are tracked on a daily basis and changes in temperature (e.g., increases or decreases) can be determined from one day to the next.

After determining the temperature of the user for each use period in the set of two or more use periods, the method 500 can include identifying at least one change in the temperature of the user between different use periods. In some cases, identifying at least one change in the temperature of the user includes identifying that the temperature of the user increases by a shift threshold, which can be a defined increase in temperature between use periods. For example, the shift threshold can be defined as an increase in temperature of 0.2 degrees Celsius or more from one use period to the next use period. In other cases, the shift threshold can be defined as a temperature increases that occur over more than two days. For example, the shift threshold can be defined as three consecutive use periods that have temperatures that are 0.1 degrees Celsius higher than the previous six use periods. In other examples, the shift threshold can be defined as a three day period having a 0.2 degree Celsius increase as compared to the maximum of the previous six days. The shift threshold can also be individually configured and/or trained for each user. For example, temperature data from multiple months could be analyzed and combined with other data such as a period start date to train the shift detection to an individual user.

In some cases, temperature measurements from multiple sensors that are within the use period can be analyzed to determine a temperature of the user for the sleep period. This can include calculating a percentile of the temperature measurements, determining an average, or performing other statistical analysis.

At 510, the method 500 can include estimating an ovulation day based on a comparison of temperatures from each sleep period. This can include determine an increase in the determined temperature of the user for one or more consecutive days. In some cases, pattern analysis, machine learning, or other analysis can be performed to determine a day or range of days that ovulation likely occurred based on an increase in the determined temperature of the user.

At 512, the method 500 can include predicting a next period start date and/or a next ovulation day of the user based on at least one previously estimated ovulation day. In some cases, BBT analysis as described herein can be performed for one or more menstrual cycles. Determined lengths of the menstrual cycles, ovulation timing and so on from previously tracked menstrual cycles can be analyzed and used to predict a start date for a next menstrual cycle, an next period start date and/or an ovulation date for a next menstrual cycle, length of a next menstrual cycle, and so on.

Figure 6:
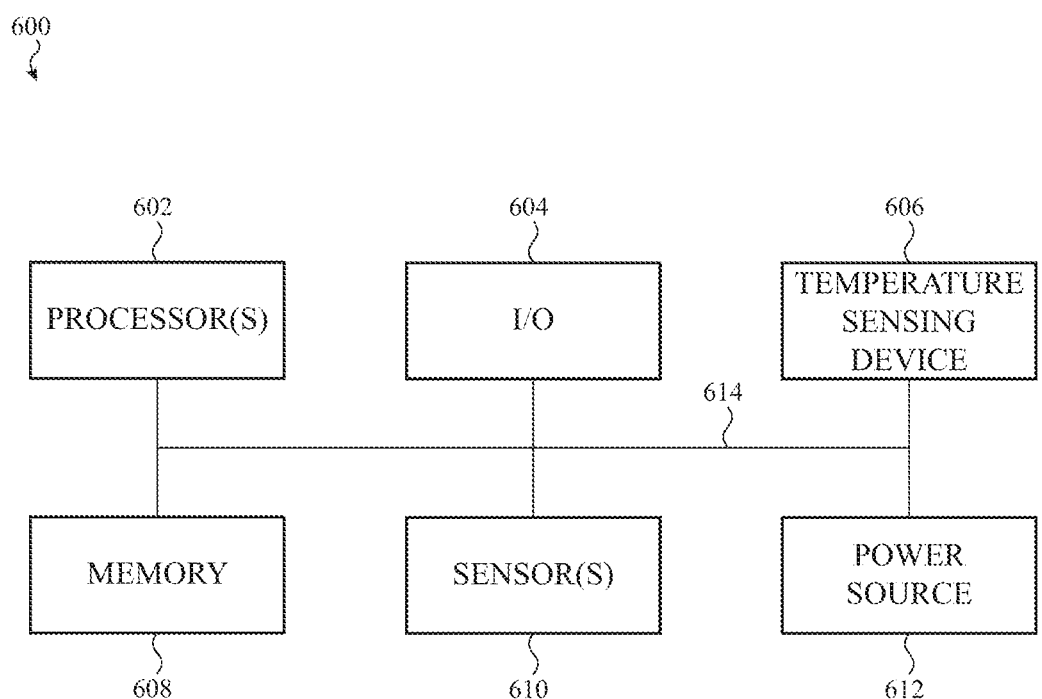
FIG. 6 is an example block diagram of a temperature sensing system for menstrual cycle tracking.

FIG. 6 is an example block diagram of a temperature sensing system 600 for menstrual cycle tracking, which can take the form of any of the temperature sensing systems as described with references to FIGS. 1-5. The temperature sensing system 600 can include a processor 602, an input/output (I/O) mechanism 604 (e.g., an input/output device, such as a touch screen, crown or button, input/output port, or haptic interface), one or more temperature sensing device 606, memory 608, other sensors 610 (e.g., an optical sensing system, barometric pressure sensors, etc.), and a power source 612 (e.g., a rechargeable battery). The processor 602 can control some or all of the operations of the temperature sensing system 600. The processor 602 can communicate, either directly or indirectly, with some or all of the components of the temperature sensing system 600. For example, a system bus or other communication mechanism 614 can provide communication between the processor 602, the I/O mechanism 604, the temperature sensing device 606, the memory 608, the sensors 610, and the power source 612.

The processor 602 can be implemented as any electronic device capable of processing, receiving, or transmitting data or instructions. For example, the processor 602 can be a microprocessor, a central processing unit (CPU), an application-specific integrated circuit (ASIC), a digital signal processor (DSP), or combinations of such devices. As described herein, the term "processor" is meant to encompass a single processor or processing unit, multiple processors, multiple processing units, or other suitable computing element or elements.

It should be noted that the components of the electronic device 600 can be controlled by multiple processors. For example, select components of the temperature sensing system 600 (e.g., a sensor 610) may be controlled by a first processor and other components of the temperature sensing system 600 and other component of the temperature sensing system 600 (e.g., the temperature sensing device 606) may be controlled by a second processor, where the first and second processors may or may not be in communication with each other.

The I/O device 604 can transmit and/or receive data from a user or another electronic device. An I/O device can include a display, a touch-sensing input surface, one or more buttons (e.g., a graphical user interface "home" button), one or more cameras, one or more microphones or speakers, one or more ports, such as a microphone port, and/or a keyboard. Additionally or alternatively, an I/O device 604 or port can transmit electronic signals via a communications network, such as a wireless and/or wired network connection. Examples of wireless and wired network connections include, but are not limited to, cellular, Wi-Fi, Bluetooth, IR, and Ethernet connections.

The temperature sensing device 606 can be any of, or include a combination of features of the temperature sensing devices described herein, such as temperature sensing devices 102, 200, 302. In some cases, the temperature sensing system 600 can include multiple temperature sensing devices 606.

The memory 608 can store electronic data that can be used by the temperature sensing system 600. For example, the memory 608 can store electrical data or content such as, for example, audio and video files, documents and applications, device settings and user preferences, timing signals, control signals, and data structures or databases. The memory 608 can be configured as any type of memory. By way of example only, the memory 608 can be implemented as random access memory, read-only memory, Flash memory, removable memory, other types of storage elements, or combinations of such devices.

The temperature sensing system 600 may also include one or more sensors 610 positioned almost anywhere on the electronic device 600. The sensor(s) 610 can be configured to sense one or more types of parameters, such as but not limited to, pressure, light, touch, heat, movement, relative motion, biometric data (e.g., biological parameters), and so on. For example, the sensor(s) 610 may include a heat sensor, a position sensor, a light or optical sensor, an accelerometer, a pressure transducer, a gyroscope, a magnetometer, a health monitoring sensor, and so on. Additionally, the one or more sensors 610 can utilize any suitable sensing technology, including, but not limited to, capacitive, ultrasonic, resistive, optical, ultrasound, piezoelectric, and thermal sensing technology.

The power source 612 can be implemented with any device capable of providing energy to the temperature sensing system 600. For example, the power source 612 may be one or more batteries or rechargeable batteries. Additionally or alternatively, the power source 612 can be a power connector or power cord that connects the temperature sensing system 600 to another power source, such as a wall outlet.

The foregoing description, for purposes of explanation, used specific nomenclature to provide a thorough understanding of the described embodiments. However, it will be apparent to one skilled in the art that the specific details are not required in order to practice the described embodiments. Thus, the foregoing descriptions of the specific embodiments described herein are presented for purposes of illustration and description. They are not targeted to be exhaustive or to limit the embodiments to the precise forms disclosed. It will be apparent to one of ordinary skill in the art that many modifications and variations are possible in view of the above teachings.

What is claimed is:

1. A method for tracking a menstrual cycle of a user, the method comprising:
receiving temperature measurements from an array of temperature sensors positioned on a temperature sensing device, wherein the temperature sensing device is configured to contact the user while the user is sleeping;
determining a set of two or more use periods for the array of temperature sensors wherein, for each use period of the set of two or more use periods, temperature measurements from at least one temperature sensor of the array of temperature sensors exceeds a first temperature threshold for a duration;
identifying, for each use period of the set of two or more use periods, a set of temperature measurements that are within a same use period and exceed a second temperature threshold;
for each use period in the set of two or more use periods, determining a temperature of the user using the set of temperature measurements from a respective use period;
after determining the temperature of the user for each use period in the set of two or more use periods, identifying at least one change in the temperature of the user between different use periods; and
estimating an ovulation day of the user based on the at least one change in the temperature of the user.

2. The method of claim 1, wherein:
identifying the set of temperature measurements comprises identifying temperature measurements from the same use period that are below a third temperature threshold;
determining the temperature of the user comprises using temperature measurements from the set of temperature measurements that fall within a percentile range; and
identifying the at least one change in the temperature of the user includes identifying that the temperature of the user increases by a shift threshold.

3. The method of claim 2, wherein:
the second temperature threshold is greater than the first temperature threshold;
the second temperature threshold is lower than a typical body temperature; and
the third temperature threshold is greater than the typical body temperature.

4. The method of claim 1, wherein estimating the ovulation day of the user comprises determining at least two use periods in the set of two or more use periods where the temperature of the user is at least 0.1 degrees Celsius higher than two previous use periods in the set of two or more use periods.

5. The method of claim 1, wherein estimating the ovulation day of the user comprises determining at least one use period in the set of two or more use periods where the temperature of the user is at least 0.2 degrees Celsius higher than a maximum temperature of two previous use periods.

6. The method of claim 1, wherein determining the temperature of the user comprises averaging the set of temperature measurements.

7. The method of claim 1, wherein determining the temperature of the user comprises determining an eighty-fifth percentile of the set of temperature measurements.

8. The method of claim 1, further comprising predicting a next period start date for the user at least partially based on the estimated ovulation day.

9. The method of claim 1, wherein determining the set of two or more use periods comprises, for each use period of the set of two or more use periods, determining that temperature measurements from a first or a second temperature sensor of the array of temperature sensor exceed the first temperature threshold for the duration; and
identifying, for each use period of the set of two or more use periods, the set of temperature measurements that are within the same use period and exceed the second temperature threshold comprises aggregating the received temperature measurements from the first and second temperature sensors.

10. A system for tracking menstrual cycles, comprising:
an array of temperature sensors positioned on a temperature sensing device, wherein the temperature sensing device is configured to contact the user while the user is sleeping; and
a processor operative to:
receive temperature measurements from the array of temperature sensors;
detect a set of two or more use periods wherein, for each use period of the set of two or more use periods, received temperature measurements from at least one of the array of temperature sensors exceed a first temperature threshold for a duration;
filter, for each use period of the set of two or more use periods, the received temperature measurements to identify a set of temperature measurements in the received temperature measurements from a same use period that exceed a second temperature threshold;
for each use period in the set of two or more use periods, determine a temperature of a user using the set of temperature measurements from a respective use period;
identify at least one change in the temperature of the user between different use periods using the determined temperature for each use period; and
estimate an ovulation day of the user based on the at least one change in the temperature of the user.

11. The system of claim 10, wherein the processor is operative to:
detect a first use period of the set of two or more use periods where received temperature measurements from a first or a second temperature sensor of the array of temperature sensor exceed the first temperature threshold for the duration; and
for the first use period, aggregate the received temperature measurements from the first and second temperature sensors.

12. The system of claim 10, wherein the array of temperature sensors are positioned in a one-dimensional array.

13. The system of claim 12, wherein temperature sensors of the array of temperature sensors are positioned between about 3 centimeters and about 6 centimeters apart.

14. The system of claim 10, wherein the array of temperature sensors are positioned in a two-dimensional array.

15. The system of claim 10, wherein the array of temperature sensors comprise one or more of a resistance temperature detector, a negative temperature coefficient detector, a thermocouple, a semiconductor temperature detector, or a combination thereof.

* * * * *